(12) United States Patent
Park

(10) Patent No.: US 11,957,430 B2
(45) Date of Patent: Apr. 16, 2024

(54) INTERNET-OF-THINGS PATCH-TYPE SENSOR DEVICE AND SENSING INFORMATION MONITORING SYSTEM AND SENSING INFORMATION MONITORING METHOD USING SAME

(71) Applicant: Ji Man Park, Daejeon (KR)

(72) Inventor: Ji Man Park, Daejeon (KR)

( * ) Notice: Subject to any disclaimer, the term of this patent is extended or adjusted under 35 U.S.C. 154(b) by 845 days.

(21) Appl. No.: 16/971,629

(22) PCT Filed: Feb. 22, 2018

(86) PCT No.: PCT/KR2018/002157
§ 371 (c)(1),
(2) Date: Aug. 20, 2020

(87) PCT Pub. No.: WO2019/164028
PCT Pub. Date: Aug. 29, 2019

(65) Prior Publication Data
US 2020/0390333 A1      Dec. 17, 2020

(30) Foreign Application Priority Data
Feb. 21, 2018   (KR) .......................... 10-2018-0020689

(51) Int. Cl.
*A61B 5/00*      (2006.01)
*G08C 17/02*    (2006.01)
*G16Y 20/30*    (2020.01)
*G16Y 20/40*    (2020.01)

(52) U.S. Cl.
CPC .......... *A61B 5/0002* (2013.01); *A61B 5/6833* (2013.01); *A61B 5/742* (2013.01); *G08C 17/02* (2013.01); *G16Y 20/30* (2020.01); *G16Y 20/40* (2020.01); *A61B 2560/0214* (2013.01); *A61B 2562/08* (2013.01)

(58) Field of Classification Search
CPC ........ A61B 2560/0214; A61B 2562/08; G08C 17/02; G16Y 20/30; G16Y 20/40
See application file for complete search history.

(56) References Cited

U.S. PATENT DOCUMENTS

2018/0094999 A1* 4/2018 Aliyu ...................... G01M 3/04

FOREIGN PATENT DOCUMENTS

| KR | 10-2012-0065540 A | 6/2012 |
| KR | 10-2012-0087633 A | 8/2012 |
| KR | 10-2013-0030060 A | 3/2013 |
| KR | 101248190 B1 * | 3/2013 |
| KR | 20130030060 A * | 3/2013 |

(Continued)

*Primary Examiner* — Manuel L Barbee
(74) *Attorney, Agent, or Firm* — Bridgeway IP Law Group, PLLC; Sang Ho Lee; Hyun Woo Shin

(57) ABSTRACT

Provided is an Internet-of-Things patch-type sensor device and a sensing information monitoring system and a sensing information monitoring method using same, which can easily obtain sensing information from an object to be measured, such as a human body or a thing, and check state changes of the object to be measured by using the sensing information. The Internet-of-Things patch-type sensor device includes: a lower plate unit detachably coupled to an object to be measured; a control panel unit stacked and fixed on the top of the lower plate unit; and a top plate unit stacked and fixed on the top of the control panel unit.

8 Claims, 4 Drawing Sheets

(56) References Cited

FOREIGN PATENT DOCUMENTS

| | | |
|---|---|---|
| KR | 10-2014-0092486 A | 7/2014 |
| KR | 10-2017-0031547 A | 3/2017 |
| KR | 10-2017-0056933 A | 5/2017 |

* cited by examiner

INTERNET-OF-THINGS PATCH-TYPE SENSOR DEVICE AND SENSING INFORMATION MONITORING SYSTEM AND SENSING INFORMATION MONITORING METHOD USING SAME

TECHNICAL FIELD

The present disclosure relates to an Internet-of-Things (IoT) patch-type sensor device and a sensing information monitoring system and a sensing information monitoring method using the same, and more particularly, to an IoT patch-type sensor device that may easily acquire sensing information from an object to be measured, such as a human body or a thing, and a sensing information monitoring system and a sensing information monitoring method using the same.

RELATED ART

With the recent increasing interest in health, equipments for measuring health status information that includes biosignals, such as body temperature, blood pressure, blood sugar, and heart rate, are provided everywhere. Alternatively, a portable health status checking device is on the release. Further, many health status measuring applications executable on a smartphone are being developed. Accordingly, people may frequently measure their own health status and may further pay attention to their health management.

In addition, information about such measured health status may be transmitted to a server managed by a medical institution, such as, for example, a hospital, and may be used to monitor a health status, for example, whether a health status of a corresponding user is deteriorated and whether the user is infected with a specific disease.

The body temperature refers to human body information primarily important to check disease of a user and infection of the user, disease exacerbation of the disease, and a health status of the user and also refers to human body information that requires accuracy of a measured body temperature value and the promptness of an abnormality notification.

However, according to the related art, if a measurement performer needs to directly contact a thermometer with a body part of a subject to check a health status of the subject, the accuracy of measurement is guaranteed, however, there is a risk of infection. Also, although the measurement performer contacts the thermometer with the body part of the subject, the accuracy of the thermometer is not guaranteed due to an abnormal contact according to a skill level.

Also, according to the related art, a health status check of a subject is performed only when a necessity for the health status check is recognized. Therefore, there are some limitations in verifying in advance an abnormality in a body of the subject. Also, the subject may need to directly visit a hospital to verify information about a health status.

Also, according to the related art, medical information provided based on a health status, a medical service, and medical information, and a medical service providing scheme are very limited, which may cause a user inconvenience.

An example of the related art includes Korean Patent Laid-Open Publication No. 10-2017-0031547 (titled "apparatus and system for sensing body condition" and published on Mar. 21, 2017).

DETAILED DESCRIPTION

Object

The present disclosure is conceived to solve the aforementioned issues and provides an Internet-of-Things (IoT) patch-type sensor device that may easily acquire sensing information from an object to be measured, such as a human body and a thing, and may check a change in a status of the object to be measured based on the sensing information, and a sensing information monitoring system and a sensing information monitoring method using the same.

Solution

According to an example embodiment to accomplish the aforementioned objects of the present disclosure, an Internet-of-Things (IoT) patch-type sensor device according to the present disclosure includes a lower plate unit configured to detachably couple with an object to be measured; a control plate unit configured to stack and fasten on the lower plate unit; and an upper plate unit configured to stack and fasten on the control plate unit.

Here, the lower plate unit comprises contact conduction portion configured to transmit measurement information of the object to be measured through contact with the object to be measured, and the control plate unit comprises a power terminal portion configured to apply power, a wireless communication portion configured to perform wireless transmission of the measurement information and mutual communication with an outside, a sensing module configured to generate sensing information by sensing the measurement information transmitted from the contact conduction portion, an identification tag configured to embed with an identification code of the sensing module, a display module configured to display an operation status of the sensing module and a communication status of the wireless communication portion, and a controller configured to control an operation of the wireless communication portion, the sensing module, and the display module, and the upper plate unit comprises a power connector configured to connect to the power terminal portion and a display window configured to display the display module.

Here, the control plate unit further comprises an input/output (I/O) terminal portion configured to connect to the controller and to perform wired transmission of the measurement information and mutual communication with the outside.

Here, the controller comprises a request verifier configured to check a data request for the measurement information from the outside and a measurement period of the measurement information from the outside; a terminal verifier configured to check a mutual communication status with the outside; a data storage configured to store the sensing information; and a sensor verifier configured to check a power status of the sensing module and an operation status of the sensing module.

The IoT patch-type sensor device according to the present disclosure further includes a battery module configured to detachably connect to or integrally connect to the power connector for power supply.

Here, the battery module comprises a battery terminal portion configured to detachably couple with the power connector or integrally couple with the power connector to connect a battery and the power connector; a battery case provided with the battery terminal portion and to which the battery is mounted; a finishing plate portion configured to supportively surround the battery case; and a plate coupler provided to the upper plate unit and configured to fasten the battery case to the upper plate unit.

A sensing information monitoring system according to the present disclosure includes an IoT patch-type sensor device according to the present disclosure; and a monitoring device configured to mutually communicate with the sensor device and to monitor a status of the object to be measured based on the sensing information.

A sensing information monitoring method according to the present disclosure is a driving method of a sensing information monitoring system according to the present disclosure and includes a sensor registration operation of registering the sensor device to the monitoring device using the identification code of the sensing module; a data setting operation of setting the measurement information and a measurement period of the measurement information; a data request operation of requesting the sensing module for data set through the data setting operation; a data sensing operation of operating the sensor device to acquire the sensing information based on request information forwarded through the data request operation; and a data monitoring operation of monitoring a status of the object to be measured based on the sensing information acquired through the data sensing operation.

Here, the sensor registration operation comprises an app execution operation of executing a program linked to the sensor device; a sensor installation operation of activating the sensor device; a sensor pairing operation of requesting the sensor device for the identification code and registering the sensor device to the program; a device information transmission operation of receiving device information that includes a power status the sensor device, a communication status with the sensor device, sensing information of the sensing module, and display information the display module; and a device information storage operation of storing the device information.

Here, the data sensing operation comprises a request verification operation of checking request information forwarded through the data request operation; a request sensing operation of operating the sensing module based on request information forwarded through the data request operation; a terminal verification operation of checking a communication status between the sensor device and the monitoring device; and a sensor verification operation of checking a power status of the sensing module and an operation status of the sensing module.

Here, the data monitoring operation comprises a request storage operation of storing the sensing information being received; a sensor identification operation of sorting the sensing information for each identification code; a monitoring operation of visually displaying the sensing information corresponding to the identification code; and a status verification operation of checking the sensing information based on preset status information.

Effect

According to an Internet-of-Things (IoT) patch-type sensor device and a sensing information monitoring system and a sensing information monitoring method using the same according to the present disclosure, it is possible to easily acquire sensing information from an object to be measured, such as a human body and a thing, and to check a change in a status of the object to be measured based on the sensing information.

Also, the present disclosure may allow a sensor device to be readily embedded in and contact an object to be measured and to stably sense measurement information of the object to be measured, thereby improving precision of sensing information.

Also, the present disclosure may easily acquire an identification code of a sensor device and may securely register the sensor device to a monitoring device.

Also, the present disclosure enables wired communication with a monitoring device as well as wireless communication with the monitoring device and may securely transmit data stored in a sensor device, thereby stabilizing monitoring of sensing information.

Also, the present disclosure may readily check a status of a sensor device, may support smooth data transmission between the sensor device and a monitoring device, and, if an error occurs, may allow a wearer of the sensor device and a user of the monitoring device to verify the error of the sensor device in real time.

Also, the present disclosure may stably supply power to be applied to a sensor device and to prevent an operation of the sensor device from being suspended.

Also, the present disclosure may facilitate replacement and attachment and detachment of a battery with respect to a sensor device and to extend a lifespan of the battery.

MODE

Hereinafter, embodiments of an Internet-of-Things (IoT) patch-type sensor device and a sensing information monitoring system and a sensing information monitoring method according to the present disclosure are described. Here, the present disclosure is not limited thereto or restricted thereby. Also, detailed description related to a known function or configuration in describing the present disclosure may be omitted for clarity of the present disclosure.

An IoT patch-type sensor device according to an embodiment of the present disclosure is described to apply to a sensing information monitoring system according to an embodiment of the present disclosure, and a sensing information monitoring method according to an embodiment of the present disclosure is described to employ a sensing information monitoring system according to an embodiment of the present disclosure.

Figure 1:
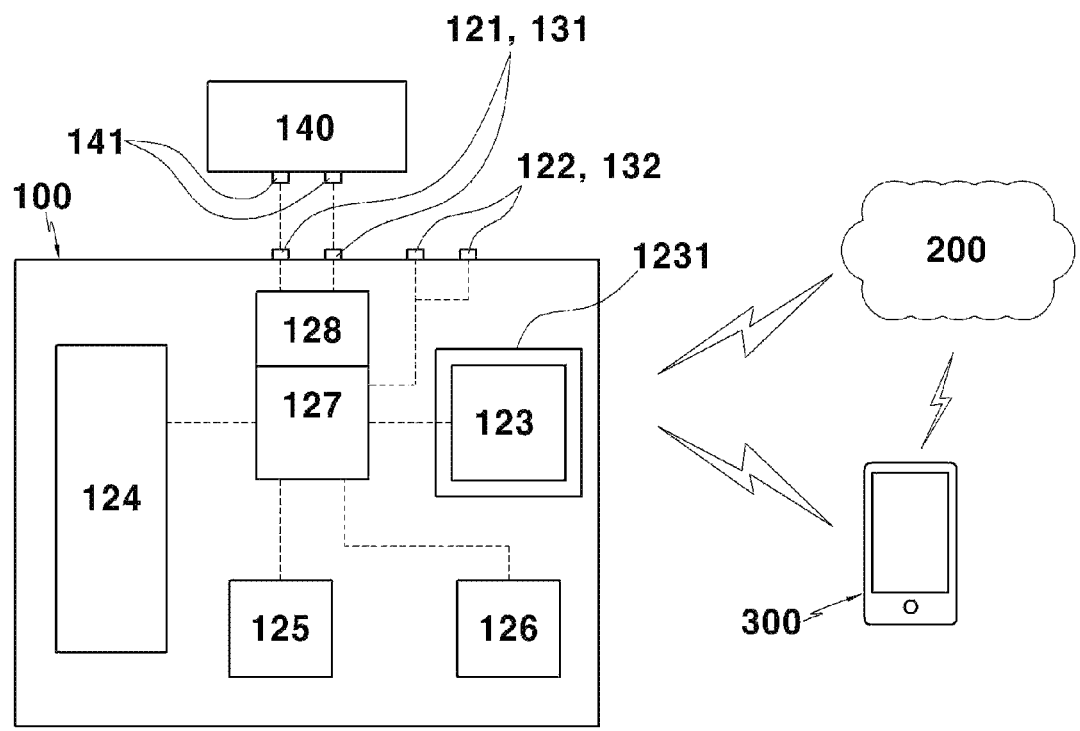
FIG. 1 illustrates a sensing information monitoring system according to an embodiment of the present disclosure.
Figure 2:
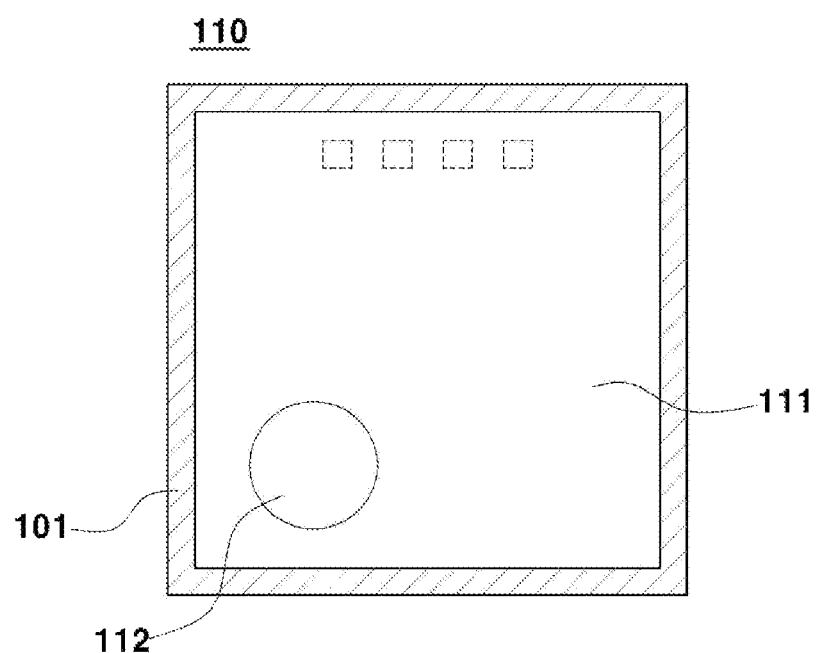
FIG. 2 is a bottom view illustrating a lower plate unit in an Internet-of-Things (IoT) patch-type sensor device according to an embodiment of the present disclosure.

Referring to FIG. 1, a sensing information monitoring system according to an embodiment of the present disclosure includes a sensor device 100 configured to directly or indirectly mount to an object to be measured, such as a human body or a thing, and to acquire sensing information therefrom and a monitoring device configured to check a change in the sensing information transmitted from the sensor device 100.

Here, the sensor device 100 may be configured as an IoT patch-type sensor device according to an embodiment of the present disclosure. The sensor device 100 may represent various types depending on an object that is to be measured. Here, a type of the sensor device 100 is not limited. At least one sensor device 100 may be provided to be spaced apart from each other at predetermined intervals and may connect to a single monitoring device.

For example, as a device that measures bio-information of a human body that is the object to be measured, the sensor device 100 may measure bio-information, for example, body temperature, pulse, blood pressure, odor of the human body, skin humidity, etc. For example, since the sensor device 100 is mounted to a patient and measures bio-information of the patent in the medical field, it is possible to discriminate a current change in disease, to identify expected disease, and to contribute to treatment and prevention of disease of the patient.

As another example, as a device that measures status information of a thing that is the object to be measured, the sensor device 100 may measure a temperature of food. For example, the sensor device 100 may be attached to a food storage container and may implement safe food. Also, the sensor device 100 may measure a temperature of a fish tank.

As another example, the sensor device 100 may be embedded in clothing that is the object to be measured and may implement smart clothing.

An embodiment of the present disclosure describes that the sensor device 100 may acquire bio-information of a human body or status information of a thing and the sensor device 100 may perform a temperature measurement. The sensor device 100 may confine information acquired through sensing information in an embedded sensing module 124.

Referring now to FIGS. 2-5, the sensor device 100 may include a lower plate unit 110, a control plate unit 120, and an upper plate unit 130, and may further include a battery module 140.

The sensor device 100 may be embedded in clothing or a thing worn around the human body or may detachably couple therewith. The sensor device 100 may be detachably attached to the human body or the thing.

Here, at least the lower plate unit 110 among the lower plate unit 110, the control plate unit 120, and the upper plate unit 130 may be elastically deformable to stabilize an attachment and detachment operation of the sensor device 100.

The lower plate unit 110, the control plate unit 120, and the upper plate unit 130 may be mutually stacked and fastened using a fastener. Here, a first fastener 101 is provided to the lower plate unit 110, a second fastener 102 is provided to the control plate unit 120, and a third fastener 103 is provided to the upper plate unit 130. Here, the first fastener 101 and the second fastener 102 couple with each other such that the control plate unit 120 is stacked and fastened on the lower plate unit 110, and the second fastener 102 and the third fastener 103 couple with each other such that the upper plate unit 130 is stacked and fastened on the control plate unit 120. Although it is illustrated that the first fastener 101, the second fastener 102, and the third fastener 103 are provided on the edge in a form of a ring in the units 110, 120, and 130, respectively, it is provided as an example only. Various arrangement may apply by considering a water-resistant characteristic and elastic deformation of each unit.

The lower plate unit 110 may detachably couple with the object to be measured. The lower plate unit 110 may include a contact conduction portion 112 configured to transmit measurement information of the object to be measured through direct or indirect contact with the object to be measured. The contact conduction portion 112 is exposed to an outside and facilitates transmission of the measurement information. For example, the contact conduction portion 112 may include a conductive material, such as conductive cloth and a metal having high conductivity in terms of a temperature characteristic. The conductive material may acquire reliable sensing information and may stably forward the measurement information of the object to be measured to the sensing module 124.

Here, the lower plate unit 110 may include an adhesive portion 111 provided on its bottom for attachment and detachment with the object to be measured. In particular, the lower plate unit 110 is elastically deformable and provides a cushion feeling and thus, may facilitate adhesion between the adhesive portion 111 and the object to be measured and may prohibit or prevent the lower plate unit 110 from being separated from the object to be measured. The adhesive portion 111 may be provided in various known forms depending on whether an object to which the adhesive portion 111 is to attach is a human body, clothing, a thing, disposable, or reusable. For example, the adhesive portion 111 may be based on silicon or urethane. In particular, if the adhesive portion 111 directly attaches to the human body, it is important to ensure that there are no skin troubles. Also, a water-resistant characteristic and a temperature characteristic need to be considered.

The control plate unit 120 is stacked and fastened on the lower plate unit 110. The control plate unit 120 may be elastically deformable with the lower plate unit 110 or the upper plate unit 130.

Figure 3:
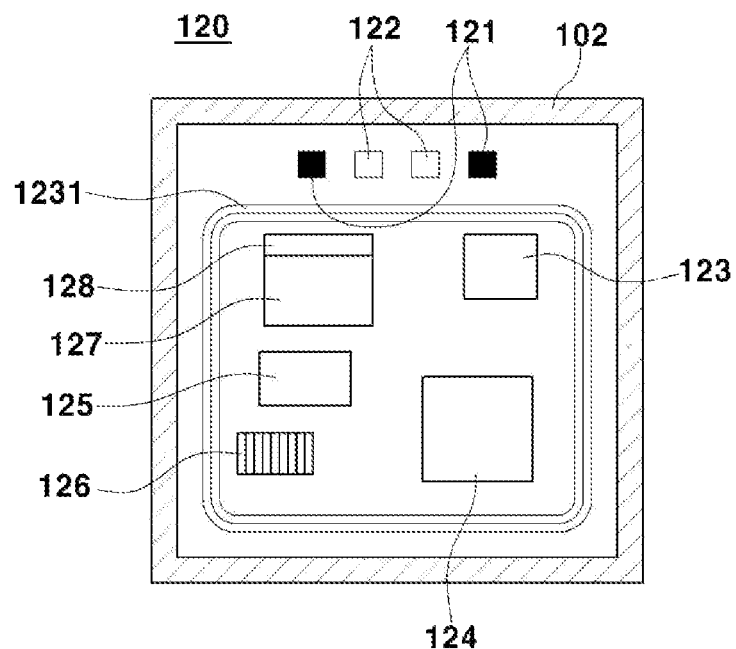
FIG. 3 is a top view illustrating a control plate unit in an IoT patch-type sensor device according to an embodiment of the present disclosure.

Referring to FIG. 3, the control plate unit 120 may include a power terminal portion 121 configured to apply power, a wireless communication portion 123 configured to perform wireless transmission of the measurement information and mutual communication with an outside, the sensing module 124 configured to generate sensing information by sensing the measurement information transmitted from the contact conduction portion 112, an identification tag configured to embed with an identification code of the sensing module 124, a display module 126 configured to display an operation status of the sensing module 124 and a communication status of the wireless communication portion 123, and a controller 127 configured to control an operation of the wireless communication portion 123, the sensing module 124, and the display module 126.

The wireless communication portion 123 may include an antenna portion 1231. The antenna portion 1231 may be formed in a form of a plurality of rings on the control plate unit 120 and arranged in a flat manner on the control plate unit 120 and accordingly, may stabilize mutual communication with the outside and may prevent wireless communication from being blocked.

The wireless communication portion 123 may perform the wireless communication using various known schemes, for example, near field communication, wireless fidelity (WiFi), Bluetooth, $3^{rd}$ generation (3G), long term evolution (LTE), and the like.

The sensing module 124 may include at least one temperature sensor configured to sense a temperature of the human body. Also, the sensing module 124 may include at least one electrocardiogram (ECG) sensor configured to conduct an ECG examination. Accordingly, the sensing module 124 may include various types of sensors in addition to the temperature sensor and the ECG sensor.

Also, the control plate unit 120 may further include an I/O terminal portion 122 configured to connect to the controller 127 and perform wired transmission of the measurement information and mutual communication with the outside.

The sensor module 124 may include various types of sensors connected in a wired manner through the I/O terminal portion 122. Here, a sensor device 100 may acquire a variety of sensing information from the connected sensors. Accordingly, a single sensor device 100 may conveniently process sensing information forwarded from the plurality of sensors through a single controller 127.

Here, a sensor arrangement interval may be adjusted in various manners to measure accurate sensing information based on heat generated from the sensor device 100.

For example, a sensor may be mounted to the armpit, belly, ear, mouth, etc., of the human body or mounted to an upper portion, a middle, portion, or a lower portion of the thing, and may acquire sensing information.

Figure 6:
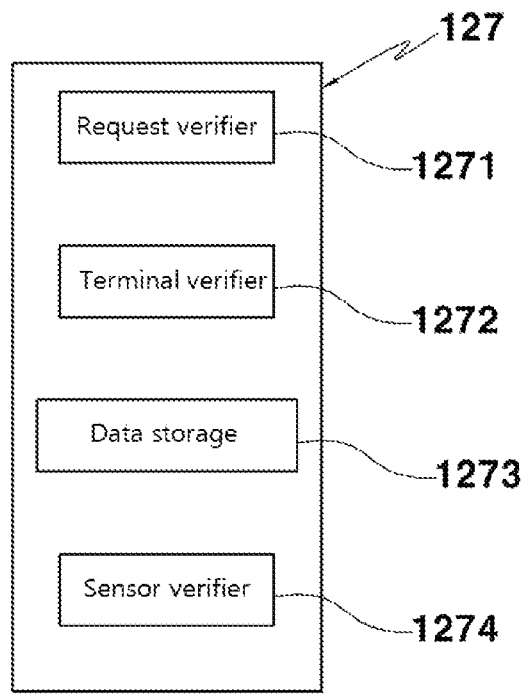
FIG. 6 is a block diagram illustrating a controller in an IoT patch-type sensor device according to an embodiment of the present disclosure.

Referring now to FIG. 6, the aforementioned controller 127 may include a request verifier 1271 configured to check a data request for the measurement information and a measurement period of the measurement information from the outside, a terminal verifier 1272 configured to check a mutual communication status with the outside, a data storage 1273 configured to store the sensing information, and a sensor verifier 1274 configured to check a power status of the sensing module 124 and an operation status of the sensing module 124.

To build a monitoring system, the terminal verifier 1272 checks a mutual communication status with the monitoring device and, if communication between the sensor device 100 and the monitoring device continues, transmits sensing information to the monitoring device.

Here, if the communication between the sensor device 100 and the monitoring device is disconnected or becomes lower than a preset intensity, the sensing information may be stored in the data storage 1273. If the communication between the sensor device 100 and the monitoring device resumes, the sensing information of the data storage 1273 may be transmitted to the monitoring device to secure the space of the data storage 1273 and to readily sort the sensing information in order of time series.

Also, if the communication between the sensor device 100 and the monitoring device is disconnected or becomes lower than the preset intensity, the sensing information may be displayed on the sensor device 100 based on a preset sensor value. That is, although the monitoring device is absent, the sensor device 100 may autonomously check a status according to the sensing information.

If the sensing information is deviated from the preset sensor value, it is variously indicated on the display module 126 of the sensor device 100. That is, a number, a light color (LED), a vibration, and sound (voice) may inform a situation according to the sensing information. For example, if a sensing temperature is higher than a preset temperature, it may be indicated in red. If the sensing temperature is lower than or equal to the preset temperature, it may be indicated in green.

The display module 126 may be described using vibration, sound, etc., depending on a service application. The display module 126 may be set to react according to the sensing information.

The preset sensor value may be input to the monitoring device in a communication status between the sensor device 100 and the monitoring device. For example, the preset sensor value may be set by a control program of the server 200 or may be set by a user app of a portable terminal 300. Therefore, the situation according to the sensing information may be quickly checked for a user desired sensor value. That is, there is provided the sensor device 100 customized for the user convenience.

Also, the controller 127 may further include a switch 128. The switch 128 may stabilize the power and communication status input from the outside by switching the power applied from the power terminal portion 121.

Figure 4:
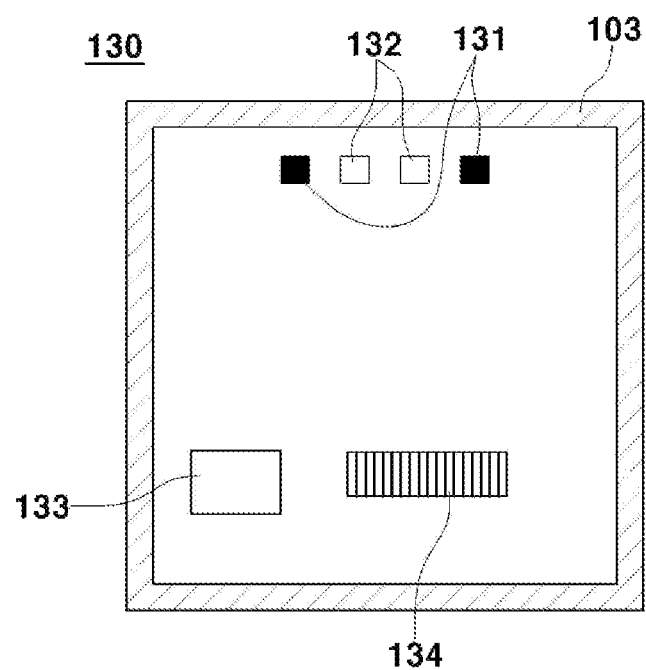
FIG. 4 is a top view illustrating an upper plate unit in an IoT patch-type sensor device according to an embodiment of the present disclosure.
Figure 5:
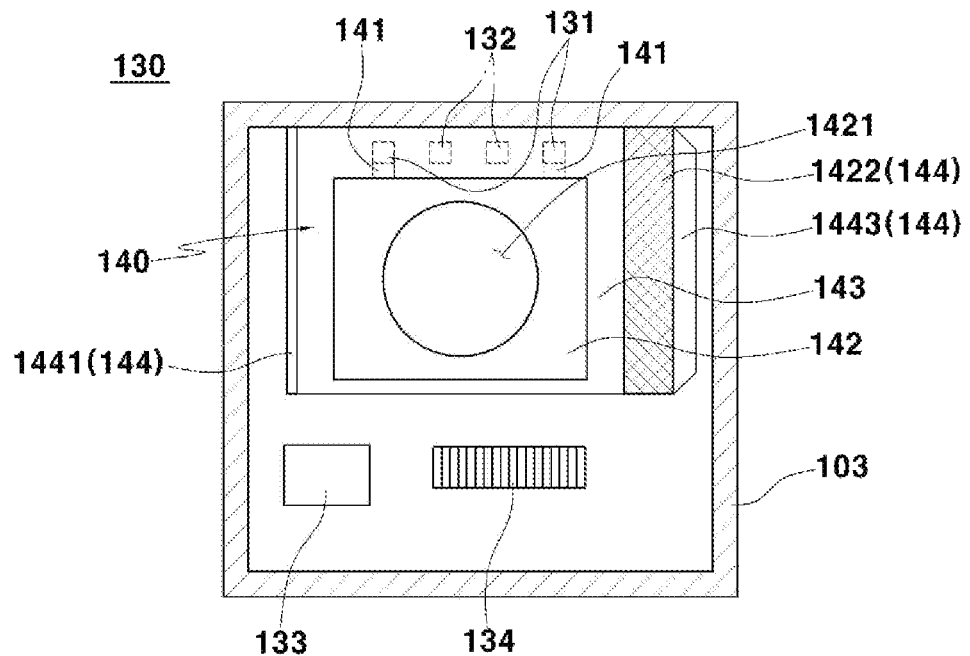
FIG. 5 is a top view illustrating a modification example of an upper plate unit in an IoT patch-type sensor device according to an embodiment of the present disclosure.

Referring to FIGS. 4-5, the upper plate unit 130 is stacked and fastened on the control plate unit 120. The upper plate unit 130 may be elastically deformable with the control plate unit 120 or the lower plate unit 110.

The upper plate unit 130 may include a power connector 131 configured to connect to the power terminal portion 121 and a display window 133 configured to expose the display module 126.

Also, the upper plate unit 130 may further include an I/O connector 132 corresponding to the I/O terminal portion 122. The I/O connector 132 may stabilize wired communication with the outside through connection to the I/O terminal portion 122.

Also, the upper plate unit 130 may include an identification code portion 134 configured to display an identification code corresponding to an identification tag 125 and to forward the identification code of the sensing module 124 to the outside. The monitoring device may acquire the identification code of the sensor device 100 by tagging of the identification code portion 134 through the portable terminal 300 in the monitoring device. The identification code portion 134 may be used if the identification code is not transmittable or needs to be directly acquired due to a failure of the identification tag 125.

The battery module 140 detachably connects to or integrally connects to the power connector 131 for power supply. The battery module 140 may integrally or detachably couple with a battery.

The battery module 140 may include a battery terminal portion 141 configured to detachably couple with the power connector 131 or integrally couple with the power connector 131 to connect the battery and the power connector 131, a battery case 142 provided with the battery terminal portion 141 and to which the battery is mounted, a finishing plate portion 143 configured to supportively surround the battery case 142, and a plate coupler 144 provided to the upper plate unit 130 and configured to fasten the battery case 142 to the upper plate unit 130. For example, the battery case 142 may couple with the upper plate unit 130. As another example, the battery case 142 may couple with the finishing plate portion 143. As another example, the battery case 142 may be surrounded by the finishing plate portion 143 and may fasten to the upper plate unit 130 in a status in which the battery terminal portion 141 is connected to the power connector 131.

The battery case 142 allows the battery to integrally couple with a battery receiver 1421 or to detachably couple with the battery receiver 1421 and thereby connect to the battery terminal portion 141.

The finishing plate portion 143 may be elastically deformable and may provide a cushion feeling.

For example, the plate coupler 144 may include a plate rotation shaft 1441 configured to supportively fasten one side of the finishing plate portion 143 based on the battery case 142 on the upper plate unit 130, and a plate attachment and detachment portion 1442 configured to detachably support another side of the finishing plate portion 143 based on the battery case 142 on the upper plate unit 130.

As another example, the plate coupler 144 may include the plate attachment and detachment portion 1442 configured to detachably support both sides of the finishing plate portion 143 based on the battery case 142 on the upper plate unit 130.

Here, various known forms, for example, Velcro, a snap, and a zipper, may apply to the plate attachment and detachment portion 1442.

Here, the plate coupler 144 may include a detachable handle 1443 configured to extend from the plate attachment and detachment portion 1442, and to allow the user to easily attach and detach the finishing plate portion 143 to and from the upper plate unit 130 by holding the detachable handle 1443.

The monitoring device mutually communicates with the sensor device 100. The monitoring device monitors a status of the object to be measured based on sensing information.

Referring back to FIG. 1, the monitoring device may include at least one of the portable terminal 300 configured to mutually communicate with the sensor device 100 and a server 200 configured to mutually communicate with the sensor device 100. The portable terminal 300 may be carried by the wearer of the sensor device 100 or the user of the monitoring device, and the server 200 may not be carried by the user. Here, if the monitoring device includes all of the portable terminal 300 and the server 200, the portable terminal 300 and the server 200 may communicate with each other and may exchange related information.

The monitoring device may include a monitoring communicator (not shown) configured to mutually communicate with the sensor device 100 through wired communication or wireless communication, a device information storage (not shown) configured to store device information (including the power status of the sensor device 100, the communication status with the sensor device 100, sensing information of the sensing module 124, and display information of the display module 126) transmitted from the sensor device 100, a sensor register (not shown) configured to register the sensor device 100 using the identification code of the sensing module 124, a data setter (not shown) configured to set an operation of the sensor device 100 based on device information, and a data monitoring portion (not shown) configured to monitor a status of the object to be measured based on the received device information and sensing information.

The sensor register includes a program configured to link to the sensor device 100 and a pairing portion configured to request the sensor device 100 for the identification code, to receive the identification code, and to register the sensor device 100 to the program.

The data setter may limit an operation of the sensor device 100 in correspondence to the sensing module 124 by setting the operation of the sensor device 100 based on the device information. Also, the data setter may generate request information for requesting the sensor device 100 for a set operation of the sensor device 100.

The data monitoring portion may include a sensor identifier configured to match and sort device information and identification information based on an identification code corresponding to the device information and the sensing information. Therefore, the device information and the sensing information may be matched and sorted in order of time series based on the identification code and the data may be securely stored in a device information storage. Also, the data monitoring portion may include a monitoring portion configured to display the device information and the sensing information corresponding to the identification code such that the user may monitor an operation of the sensor device in real time. Also, the data monitoring portion may include a status verifier configured to check the sensing information based on preset status information and accordingly, may quickly notify the user of an error of the sensing information and the device information.

Hereinafter, a sensing information monitoring method according to an embodiment of the present disclosure will be described. The sensing information monitoring method according to an embodiment of the present disclosure describes a driving method of a sensing information monitoring system according to an embodiment of the present disclosure.

The sensing information monitoring method according to an embodiment of the present disclosure may be implemented through an interacting operation between the sensor device 100 and the monitoring device.

Figure 7:
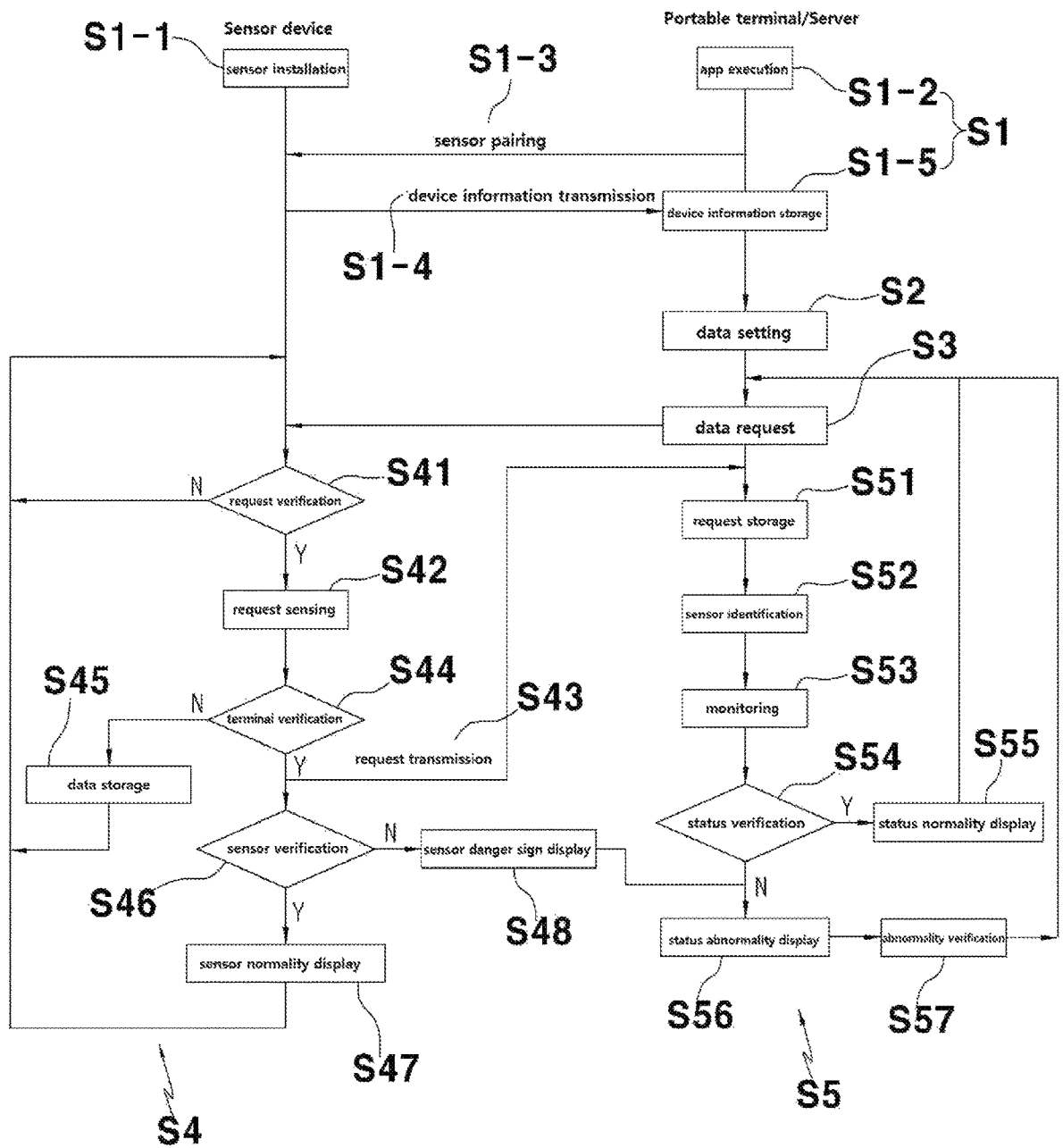
FIG. 7 is a flowchart illustrating a sensing information monitoring method according to an embodiment of the present disclosure.

Referring now to FIG. 7, the sensing information monitoring method according to an embodiment of the present disclosure includes a sensor registration operation (S1) of registering the sensor device to the monitoring device using the identification code of the sensing module 124, a data setting operation (S2) of setting the measurement information and a measurement period of the measurement information, a data request operation (S3) of requesting the sensing module 124 for data set through the data setting operation (S2), a data sensing operation (S4) of operating the sensor device 100 to acquire the sensing information based on request information forwarded through the data request operation (S3), and a data monitoring operation (S5) of monitoring a status of the object to be measured based on the sensing information acquired through the data sensing operation (S4).

The sensor registration operation (S1) may include an app execution operation (S1-2) of executing a program linked to the sensor device 100, a sensor installation operation (S1-1) of activating the sensor device 100, a sensor pairing operation (S1-3) of requesting the sensor device 100 for the identification code and registering the sensor device 100 to the program, a device information transmission operation (S1-4) of receiving device information that includes a power status the sensor device 100, a communication status with the sensor device 100, sensing information of the sensing module 124, and display information of the display module 126, and a device information storage operation (S1-5) of storing the received device information based on the identification code.

The data sensing operation (S4) may include a request verification operation (S41) of checking request information forwarded through the data request operation (S3), a request sensing operation (S42) of operating the sensing module 124 based on the request information forwarded through the data request operation (S3), a terminal verification operation (S44) of checking a communication status between the sensor device 100 and the monitoring device, and a sensor verification operation (S46) of checking a power status of the sensing module 124 and an operation status of the sensing module 124. Here, order of the request verification operation (S41), the terminal verification operation (S44), and the sensor verification operation (S46) is not limited and may be simultaneously performed through the controller 127 of the sensor device 100.

First, if the request information is received at a result of the request verification operation (S41), the request sensing operation (S42) is performed.

Also, if the request information is not received as a result of the request verification operation (S41), the request sensing operation (S42) may be performed by continuously receiving the request information or based on request information preset to the sensor device 100.

Second, if the communication status is normal as a result of the terminal verification operation (S44), a request transmission operation (S43) of transmitting the sensing information of the sensing module 124 corresponding to the request information to the outside (e.g., the monitoring device) may be performed. In the request transmission operation (S43), the sensing information stored in the data storage 1273 may be transmitted to the outside. Once the sensing information of the data storage 1273 is transmitted in the request transmission operation (S43), a data storage space may be secured by deleting the transmitted data and capacity of the data storage 1273 may be reduced.

Also, if the communication status is abnormal, for example, poor as a result of the terminal verification operation (S44), the data storage operation (S45) of storing the sensing information of the sensing module 124 corresponding to the request information may be performed. In the data storage operation (S45), a communication failure status may be displayed through the display module 126. Also, in the data storage operation (S45), the communication failure status may be forwarded to the sensor verification operation (S46).

Third, if a status of the sensing module 124 is normal as a result of the sensor verification operation (S46), the sensor device 100 may perform a sensor normality display operation (S47) of displaying a normal status on the display module 126.

Also, if the status of the sensing module 124 is abnormal, for example, poor as a result of the sensor verification operation (S46), the sensor device 100 may perform a sensor danger sign display operation (S48) of displaying an abnormal status on the display module 126. Also, in the sensor danger sign display operation (S48), the abnormal status of the sensing module 124 may be transmitted to the outside.

The data sensing operation (S4) is repeatedly performed based on the forwarded request information.

The data monitoring operation (S5) may include a request storage operation (S51) of storing the sensing information being received, a sensor identification operation (S52) of sorting the sensing information for each identification code, a monitoring operation (S53) of visually displaying the sensing information based on the identification code, and a status verification operation (S54) of checking the sensing information based on preset status information.

The sensing information stored in the request storage operation (S51) is updated based on sorting through the sensor identification operation (S52).

Here, if the sensing information is present within preset status information as a result of the status verification operation (S54), a status normality display operation (S55) of displaying that information displayed in the monitoring operation (S53) is normal may be performed.

Also, if the sensing information is out of the preset status information as a result of the status verification operation (S54), a status abnormality display operation (S56) of displaying that the information displayed in the monitoring operation (S53) is abnormal may be performed. An abnormality verification operation (S57) of alerting abnormal information may be performed after performing the status abnormality display operation (S56).

The data monitoring operation (S5) may be repeatedly performed based on information forwarded from the sensing module 124. The data monitoring operation (S5) may return to the data request operation (S3) and may continuously forward the request information to the sensing module 124.

To perform a smart service in the status verification operation (S54), a situation control service, for example, AnyCare service, may be built in the monitoring device. Also, monitoring may be performed through the monitoring operation (S53) and the status abnormality display operation (S56). Here, if the monitoring device or the data monitoring operation (S5) analyzes a change in the sensing information in a predetermined time during a process of monitoring the sensing information received from the sensor device 100 and thereby verifies an abnormal status or determines that a notification service is required, a situation of the sensing information may be primarily displayed on the portable terminal 300.

The monitoring device may represent the situation using sound (voice), vibration, and the like. For example, a button "A (Anycare)" is displayed (popped up) on the portable terminal 300 to directly contact the server 200 or a situation control center based on the sensing information while displaying the situation of the sensing information on the portable terminal 300. Here, if the user presses the button, the user may use a necessary service through connection to the server 200 or the situation control center.

Also, although the portable terminal 300 primarily analyzes the sensing information and informs the user of the sensing information, the sensing information collected by the portable terminal 300 may be transmitted to the server 200 in real time and the situation control center may contact the portable terminal 300 of the user using the sensor device 100 for a further upgraded smart service. The situation control center provides emergency information to provide countermeasures according to an emergency situation based on the sensing information of the user.

For example, emergency information may provide the user with a convenient and safe service by informing a nearest hospital and pharmacy where an emergency treatment is available or by providing a first aid method according to high fever or low body temperature, if the user is in danger due to high fever or low body temperature.

As another example, emergency information may provide the user with a convenient and safe service by informing a nearest hospital and pharmacy where an emergency treatment is available or by providing a first aid method according to a high heartrate or low heartrate, if the user is in danger due to high heartrate or low heartrate.

The sensing information monitoring system may provide various services to the user using the sensor device 100. That is, the sensing information monitoring system may provide countermeasures according to a situation through contact with the user based on sensing information and may provide the user with an optimal customized service, such as, for example, a service linked to a hospital, an emergency transportation service, and the like.

The sensing information monitoring system may provide a customized service by intelligently collecting, storing, and analyzing sensing information collected from the user and thus, may provide convenience and reliability. Also, if a large amount of sensing information is collected over a long period of time, a bigdata service may be constructed. Also, a user customized service may be primarily provided and various statistical bigdata services may be provided if a large amount of sensing information is continuously collected.

According to the aforementioned IoT patch-type sensor device and the sensing information monitoring system and the sensing information monitoring method using the same, it is possible to easily acquire sensing information from an object to be measured, such as a human body or a thing, and to check a change in a status of the object to be measured based on the sensing information.

Also, the sensor device 100 may be readily embedded in and contact the object to be measured and may stably sense measurement information of the object to be measured, thereby improving precision of sensing information.

Also, it is possible to easily acquire an identification code of the sensor device 100 and to securely register the sensor device 100 to the monitoring device.

Also, it is possible to enable wired communication with the monitoring device as well as wireless communication with the monitoring device and to securely transmit data stored in the sensor device 100, thereby stabilizing monitoring of sensing information.

Also, it is possible to readily check a status of the sensor device 100, to support smooth data transmission between the sensor device 100 and the monitoring device, and, if an error occurs, to allow a wearer of the sensor device 100 and a user of the monitoring device to verify the error of the sensor device 100 in real time.

Also, it is possible to stably supply power to be applied to the sensor device 100 and to prevent an operation of the sensor device 100 from being suspended.

Also, it is possible to facilitate replacement and attachment and detachment of the battery with respect to the sensor device 100 and to extend a lifespan of the battery.

Although the example embodiments of the present disclosure have been described with reference to the drawings, those skilled in the art may understand that various alterations or modifications may be made to the present disclosure without departing from the spirit and scope of the present disclosure as set forth in the following claims.

INDUSTRIAL APPLICABILITY

The present disclosure may directly or indirectly mount an IoT patch-type sensor device to an object to be measured, such as a human body or a thing, and may monitor a status of the object to be measured based on sensing information transmitted through the IoT patch-type sensor device. For example, if the object to be measured is a human body, the patch-type sensor device may be attached onto the skin and may acquire bio-information about a change in the human body and a monitoring system may check a health status of the human body based on the bio-information. As another example, if the object to be measured is a thing, the patch-type sensor device may be attached onto the surface of the thing and may acquire thing information about a change in the thing and the monitoring system may check a change in the status of the thing based on the thing information.

What is claimed is:

1. An Internet-of-Things (IoT) patch-type sensor device comprising:
 a lower plate unit configured to detachably couple with an object to be measured;
 a control plate unit configured to stack and fasten on the lower plate unit; and
 an upper plate unit configured to stack and fasten on the control plate unit,
 wherein the lower plate unit comprises a contact conduction portion configured to transmit measurement information of the object to be measured through contact with the object to be measured,
 wherein the control plate unit comprises a power terminal portion configured to apply power, a wireless communication portion configured to perform wireless transmission of the measurement information and mutual communication with an outside, a sensing module configured to generate sensing information by sensing the measurement information transmitted from the contact conduction portion, an identification tag configured to embed with an identification code of the sensing module, a display module configured to display an operation status of the sensing module and a mutual communication status of the wireless communication portion, and a controller configured to control an operation of the wireless communication portion, the sensing module, and the display module,
 wherein the upper plate unit comprises a power connector configured to connect to the power terminal portion and a display window configured to display the display module,
 wherein the IoT patch-type sensor device further comprises a battery module configured to detachably connect to or integrally connect to the power connector for power supply, and
 wherein the battery module comprises:
 a battery terminal portion configured to detachably couple with the power connector or integrally couple with the power connector to connect a battery and the power connector;
 a battery case provided with the battery terminal portion and to which the battery is mounted;
 a finishing plate portion configured to supportively surround the battery case; and
 a plate coupler provided to the upper plate unit and configured to fasten the battery case to the upper plate unit.

2. The IoT patch-type sensor device of claim 1, wherein the control plate unit further comprises an input/output (I/O) terminal portion configured to connect to the controller and to perform wired transmission of the measurement information and the mutual communication with the outside.

3. The IoT patch-type sensor device of claim 1, wherein the controller comprises:
 a request verifier configured to check a data request for the measurement information and a measurement period of the measurement information from the outside;
 a terminal verifier configured to check Hall the mutual communication status with the outside;
 a data storage configured to store the sensing information; and
 a sensor verifier configured to check a power status of the sensing module and the operation status of the sensing module.

4. A sensing information monitoring system comprising:
 a sensor device of claim 1; and
 a monitoring device configured to mutually communicate with the sensor device and to monitor a status of the object to be measured based on the sensing information.

5. A sensing information monitoring method that is a driving method of the sensing information monitoring system of claim 4, the sensing information monitoring method comprising:

a sensor registration operation of registering the sensor device to the monitoring device using the identification code of the sensing module;

a data setting operation of setting the measurement information and a measurement period of the measurement information;

a data request operation of requesting the sensing module for data set through the data setting operation;

a data sensing operation of operating the sensor device to acquire the sensing information based on request information forwarded through the data request operation; and a data monitoring operation of monitoring a status of the object to be measured based on the sensing information acquired through the data sensing operation.

6. The sensing information monitoring method of claim 5, wherein the sensor registration operation comprises:

an app execution operation of executing a program linked to the sensor device;

a sensor installation operation of activating the sensor device;

a sensor pairing operation of requesting the sensor device for the identification code and registering the sensor device to the program;

a device information transmission operation of receiving device information that includes a power status of the sensor device, a communication status with the sensor device, sensing information of the sensing module, and display information of the display module; and a device information storage operation of storing the device information.

7. The sensing information monitoring method of claim 6, wherein the data monitoring operation comprises:

a request storage operation of storing the sensing information being received;

a sensor identification operation of sorting the sensing information for each identification code;

a monitoring operation of visually displaying the sensing information based on the identification code; and a status verification operation of checking the sensing information based on preset status information.

8. The sensing information monitoring method of claim 5, wherein the data sensing operation comprises:

a request verification operation of checking request information forwarded through the data request operation;

a request sensing operation of operating the sensing module based on the request information forwarded through the data request operation;

a terminal verification operation of checking a communication status between the sensor device and the monitoring device; and a sensor verification operation of checking a power status of the sensing module and the operation status of the sensing module.

* * * * *